(12) United States Patent
Liu et al.

(10) Patent No.: US 8,720,266 B2
(45) Date of Patent: May 13, 2014

(54) MEASURING DEVICE

(71) Applicants: Wei Liu, Shenzhen (CN); Xue-Dong Tang, Shenzhen (CN)

(72) Inventors: Wei Liu, Shenzhen (CN); Xue-Dong Tang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/631,888

(22) Filed: Sep. 29, 2012

(65) Prior Publication Data

US 2013/0233090 A1  Sep. 12, 2013

(30) Foreign Application Priority Data

Mar. 7, 2012 (CN) .......................... 2012 1 0058058

(51) Int. Cl.
*G01L 1/04* (2006.01)

(52) U.S. Cl.
USPC ...................................... 73/161; 73/862.451

(58) Field of Classification Search
CPC .............. G01N 2203/0292; G01N 2203/0288; G01N 3/108; G01N 3/16; G01L 1/04; G01L 1/046; G01L 1/042; G01L 1/048
USPC .............. 73/161, 862.636, 862.451, 862.621, 73/862.641, 818, 862.637
See application file for complete search history.

(56) References Cited

U.S. PATENT DOCUMENTS

| 2,182,519 | A | * | 12/1939 | Handy et al. | ..................... 73/161 |
| 2,518,408 | A | * | 8/1950 | Weyand | .......................... 73/161 |
| 2,765,655 | A | * | 10/1956 | Lester | .............................. 73/161 |
| 2,799,162 | A | * | 7/1957 | Carlson | ........................... 73/161 |
| 3,138,020 | A | * | 6/1964 | Love et al. | ...................... 73/161 |
| 3,253,463 | A | * | 5/1966 | Larson | ............................. 73/161 |
| 3,420,090 | A | * | 1/1969 | Saddoris et al. | ..................... 73/9 |
| 6,094,980 | A | * | 8/2000 | Larson et al. | ................... 73/161 |

* cited by examiner

*Primary Examiner* — Lisa Caputo
*Assistant Examiner* — Jonathan Dunlap
(74) *Attorney, Agent, or Firm* — Novak Druce Connolly Bove + Quigg LLP

(57) ABSTRACT

A measuring device for measuring the torque of a torsion spring, includes a base, an electronic scale secured to the base, a supporting plate fixed to the base, and a holding mechanism slidably secured to the supporting plate. The holding mechanism includes a screw slidably secured to the supporting plate, two nuts engaging with the screw and arranged at opposite sides of the screw, and a holding portion for holding the torsion spring. The nuts are operated to adjust the height of the screw relative to the supporting plate, to drive the torsion spring to depress the electronic scale. The electronic scale displays a weight value for calculating the torque of the torsion spring when depressed by the torsion spring.

13 Claims, 5 Drawing Sheets

MEASURING DEVICE

BACKGROUND

1. Technical Field

The present disclosure relates to measuring devices, and particularly to a measuring device for measuring torque of a torsion spring.

2. Description of Related Art

Elastic members, such as torsion springs, are widely used in manufacturing process of electronic devices. Different structures and/or components of electronic devices always mate with various torsion springs. The torque of torsion springs are measured for determining whether the torsion springs is suitable. However, the torque and whether or not the torsion spring is deformed is tested by hand, which is inaccurate.

Therefore, there is room for improvement in the art.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the five views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
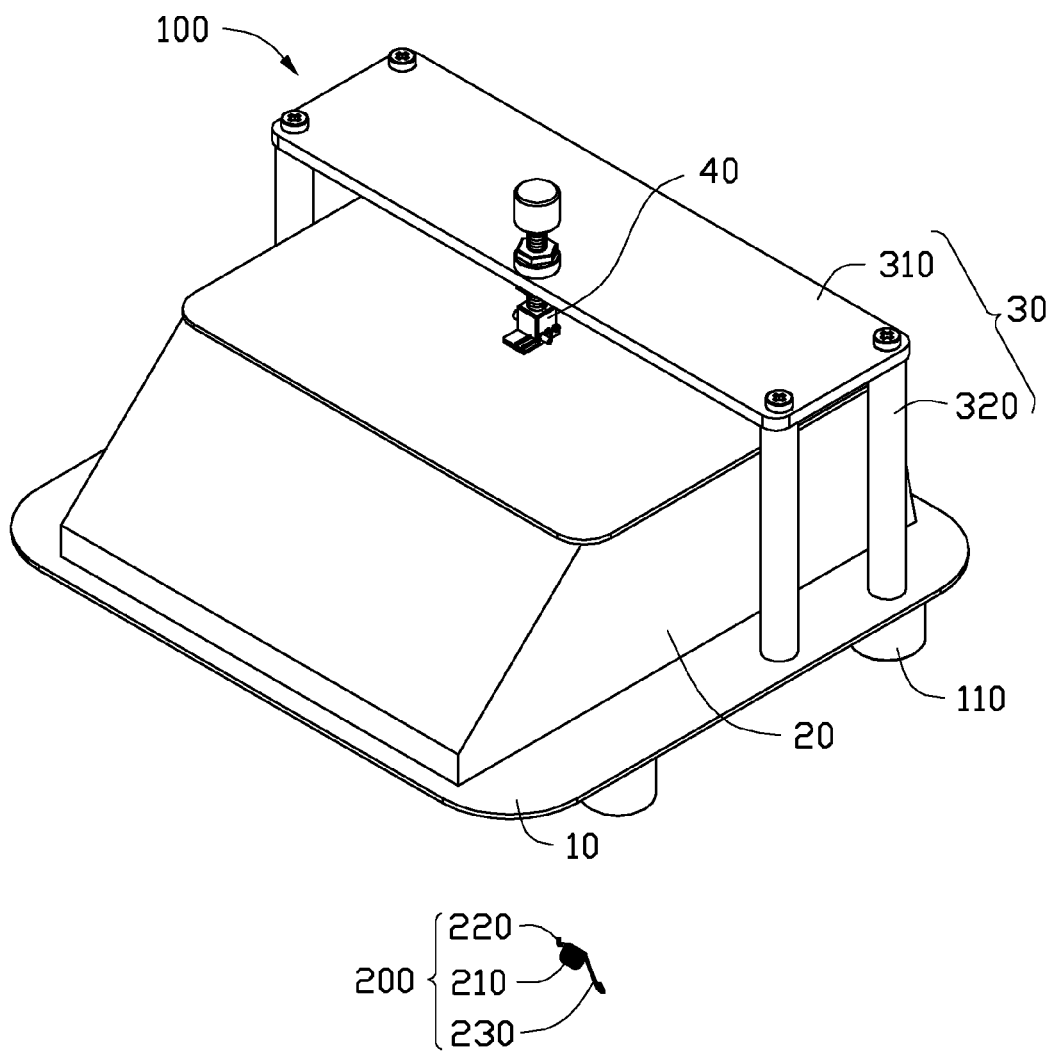
FIG. 1 is a perspective view of a measuring device for measuring torque of a torsion spring in accordance with an embodiment.

Referring to FIG. 1, a measuring device 100 for measuring torque of a torsion spring 200 is shown. The measuring device 100 includes a base 10, an electronic scale 20 mounted on the base 10, a bracket 30 fixed to the base 10 and arranged over and partially around the electronic scale 20, and a holding mechanism 40 secured to the bracket 30 for holding the torsion spring 200.

The torsion spring 200 includes a hollow main body 210, and first and second arms 220, 230 extending from opposite ends of the main body 210. In the embodiment, the main body 210 is a helical spring, the projects of the first and second arms 220,230 on a plane perpendicular to the main body 210 form an obtuse angle.

Figure 2:
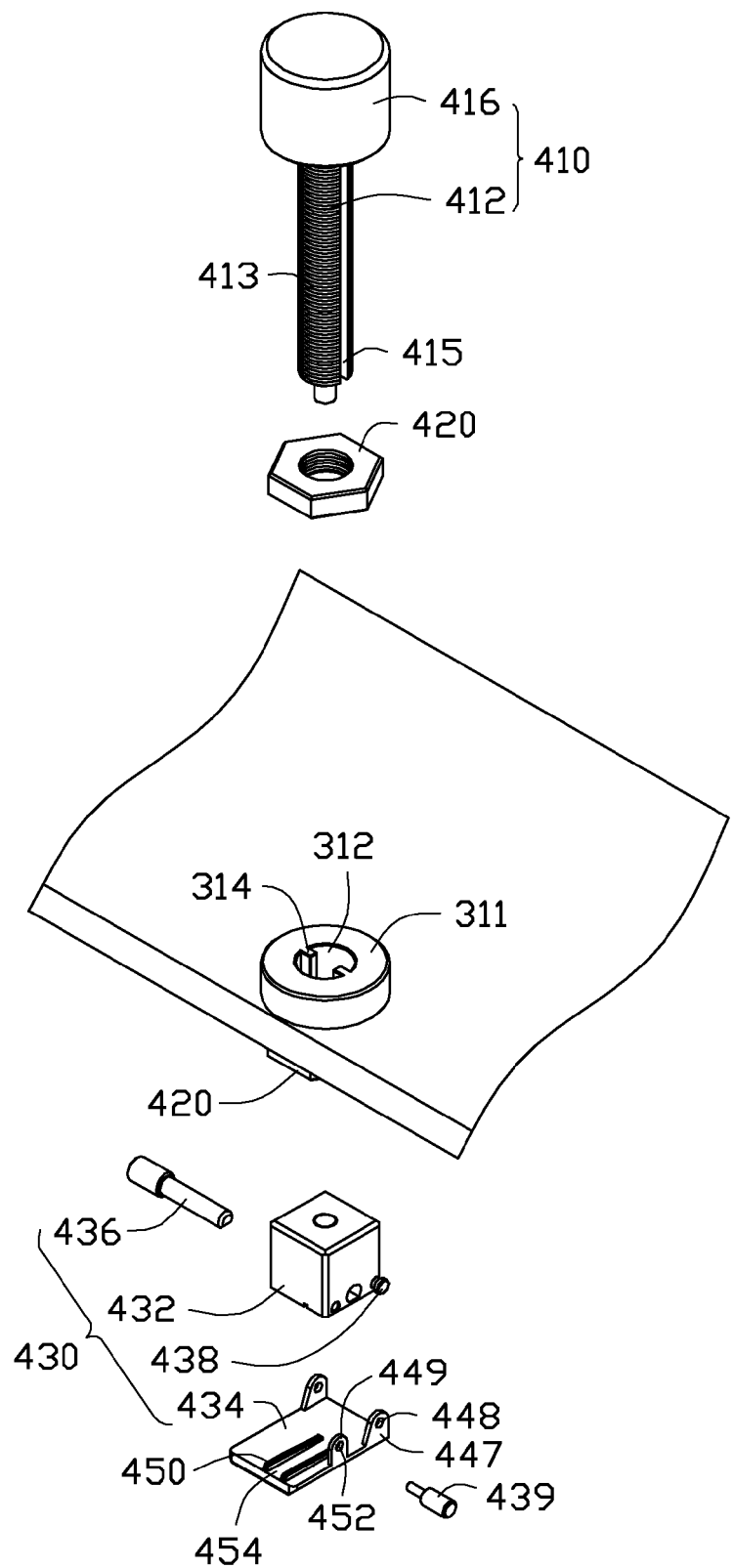
FIG. 2 is a partially disassembled view of the measuring device of FIG. 1.
Figure 3:
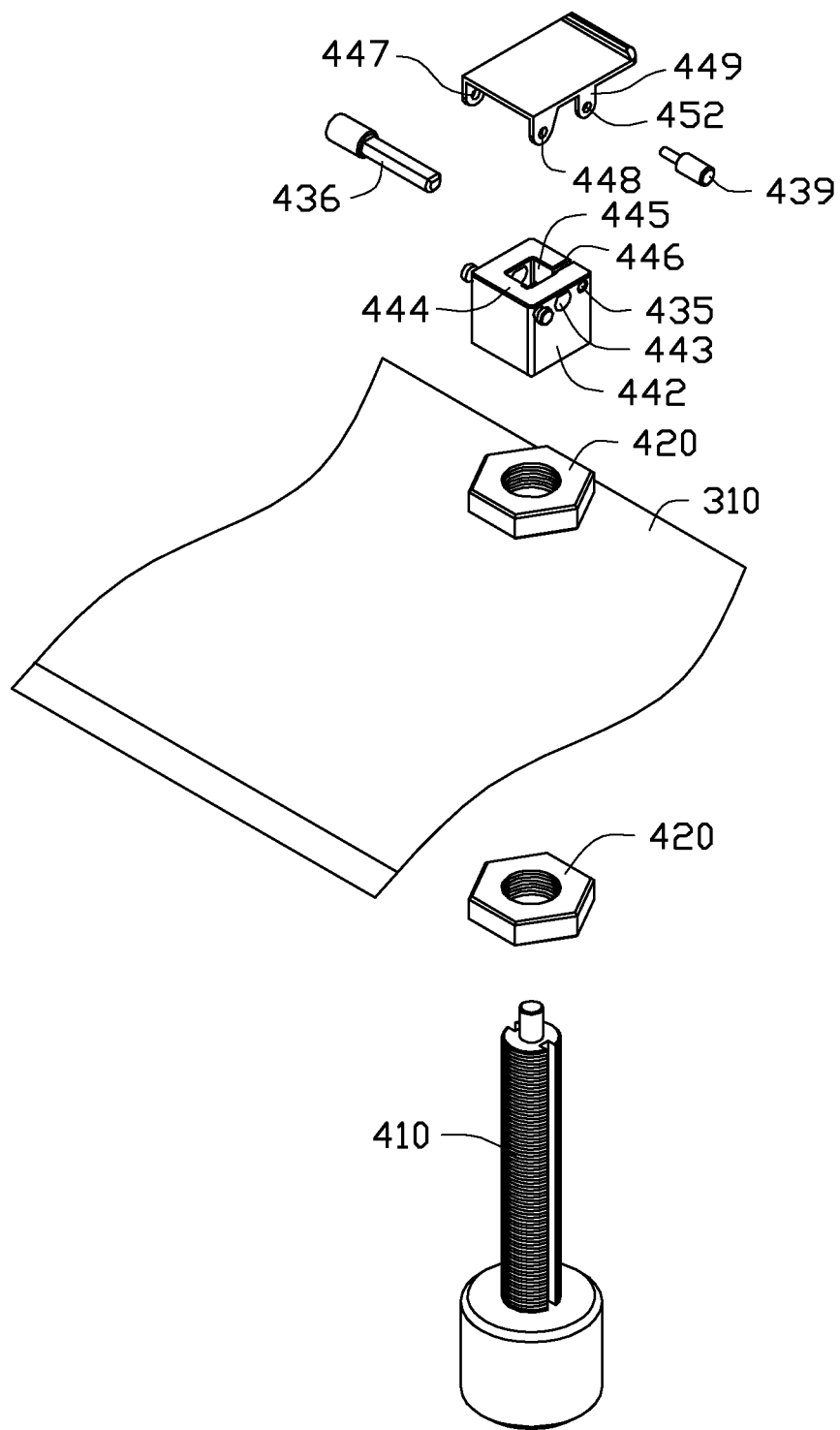
FIG. 3 is similar to FIG. 2, but viewed from another aspect.

Referring also to FIGS. 2-3, the base 10 is substantially rectangular, and is adapted to support the measuring device 100 on a supporting surface, such as a table. Four supporting posts 110 are fixed to four vertexes of the base 10.

The electronic scale 20 is mounted on a surface of the base 10 opposite to the supporting posts 110. The electronic scale 20 is adapted to measure the weight of an object. In the embodiment, the electronic scale 20 is adapted to measure the torque F of the torsion spring. In detail, when the torsion spring 200 is deformed to depress the electronic scale 20, a weight value W is first obtained by the electronic scale 20. The torque F is calculated according to the calculating equation: $F=W*g$; wherein W is obtained by the electronic scale 20, g is acceleration due to gravity which equal to approximately 9.8 meters per second per second.

The bracket 30 is fixed to the base 10, and is adapted to support the holding mechanism 40. The bracket 30 includes a supporting plate 310 and four fixing posts 320. The fixing posts 320 are perpendicularly fixed to the base 10, and are evenly arranged at opposite sides of the electronic scale 20. The length of the fixing posts 320 is greater than the height of the electronic scale 20 relative to the base 10. The supporting plate 310 is secured to opposite ends of the fixing posts 320 away from the base 10. The supporting plate 310 is over and partially around the electronic scale 20 and is substantially parallel to the base 10. A limiting post 311 is fixed to a middle of the supporting plate 310. The limiting post 311 defines a through hole 312 extending through the supporting plate 310. The through hole 312 is substantially round, and extends in a direction perpendicular to the supporting plate 310. Two protrusions 314 are symmetrically arranged on opposite sides of the inner surface of the through hole 312.

The holding mechanism 40 includes an operating post 410, two nuts 420 engaging with the operating post 410, and a holding portion 430 secured to an end of the operating post 410. The operating post 410 includes a screw 412 and an operating button 416 fixed to an end of the screw 412 away from the holding portion 430. The screw 412 is substantially cylindrical, and is slidably received in the through hole 312. The diameter of the screw 412 is slightly less than the diameter of the through hole 312. The screw 412 defines a plurality of threads 143 engaging with the nuts 420. Opposite sides of the screw 412 further define two limiting slots 415. The limiting slots 415 extend in a direction parallel to the length of the screw 412, and are adapted to receive the protrusions 314 when the screw 412 is received in the through hole 312. The limiting slots 415 engage with the protrusions 314 for preventing the screw 412 from rotating when the screw 412 slides relative to the supporting plate 310.

The nuts 420 engage with the screw 412. The size of each nut 420 is greater than the size of the through hole 312. The nuts 420 are adapted to drive the screw 412 to slide relative to the supporting plate 310, to increase and/or decrease the height of the screw 412 relative to the supporting plate 310.

To increase the height of the screw 412 relative to the supporting plate 310: first, the nut 420 above the supporting plate (referred herein as the top nut) is unscrewed for a few or more than a few threads depending on the intended height to be increased; Second, the nut 420 under the supporting plate 310 (referred herein as the bottom nut) is rotated in a first direction (for example, anticlockwise), because the bottom nut is stopped by the supporting plate 310, the screw 412 is driven to move upward, and the height of the screw 412 relative to the supporting plate 310 is increased. After the height of the screw 412 is adjusted to a desired position, the top nut is operated to abut the supporting plate 310, and cooperates with the bottom nut to position the screw 412 in the desired position.

To decrease the height of the screw 412 relative to the support base 310: first, the bottom nut is unscrewed for a few or more threads; Second, the top nut is rotated in a second direction opposite to the first direction (for example, clockwise), because the top nut is stopped by the support base 310, the screw 412 is driven to move downward, and the height of the screw 412 relative to the support base 310 is decreased. After the height of the screw 412 is decreased to a desired position, the bottom nut is operated to abut the supporting plate 310, and cooperates with the top nut to position the screw 412 in the desired position.

The holding portion 430 is adapted to hold the torsion spring 200. The holding portion 430 includes a housing 432, a clipping plate 434, a positioning post 436 detachably secured to the housing 432, and a shaft 438. The housing 432 is substantially a hollow rectangular box. The housing 432 includes a body 442 and a bottom case 444 engaging with the body 442. The body 442 is fixed to an end of the screw 412 away from the operating button 416. The body 442 defines two round holes 443 aligned parallel to the shaft 438. The body 442 further defines a latching hole 435. The latching hole 435 and the shaft 438 are arranged at opposite sides of the round holes 443. The middle of the bottom case 444 defines a substantially rectangular opening 445. An end of the bottom case 444 away from the shaft 438 further defines a receiving slot 446 communicating with the opening 445. The receiving slot 446 extends in a direction perpendicular to the shaft 438 and is adapted to receive one of the first and second arms 220, 230 when the torsion spring 200 is held in the holding portion 430.

The positioning post 436 is detachably received in the round holes 443. The positioning post 436 is extendable through the main body 210 of the torsion spring 200 to hold the torsion spring 200 to the holding portion 430.

The clipping plate 434 is substantially rectangular and is rotatably coupled to the shaft 438. Two bearings 447 are secured to an end of the clipping plate 434. The bearings 447 define two corresponding shaft holes 448 for receiving the shafts 438. A latching member 449 and two flanges 450 are further secured to the clipping plate 450. The latching member 449 defines a limiting hole 452 corresponding to the latching hole 435. The latching member 449 protrudes from a lengthwise rim of the clipping plate 450. The flanges 450 are parallel to the lengthwise rim of the clipping plate 450. The flanges 450 are spaced apart from each other to form a limiting groove 454 for receiving one of the first and second arms 220, 230.

The holding portion 430 further includes a latching post 439. The latching post 439 is detachably inserted into the limiting hole 452 and the latching hole 435 for latching the clipping plate 434 to the housing 442.

Figure 4:
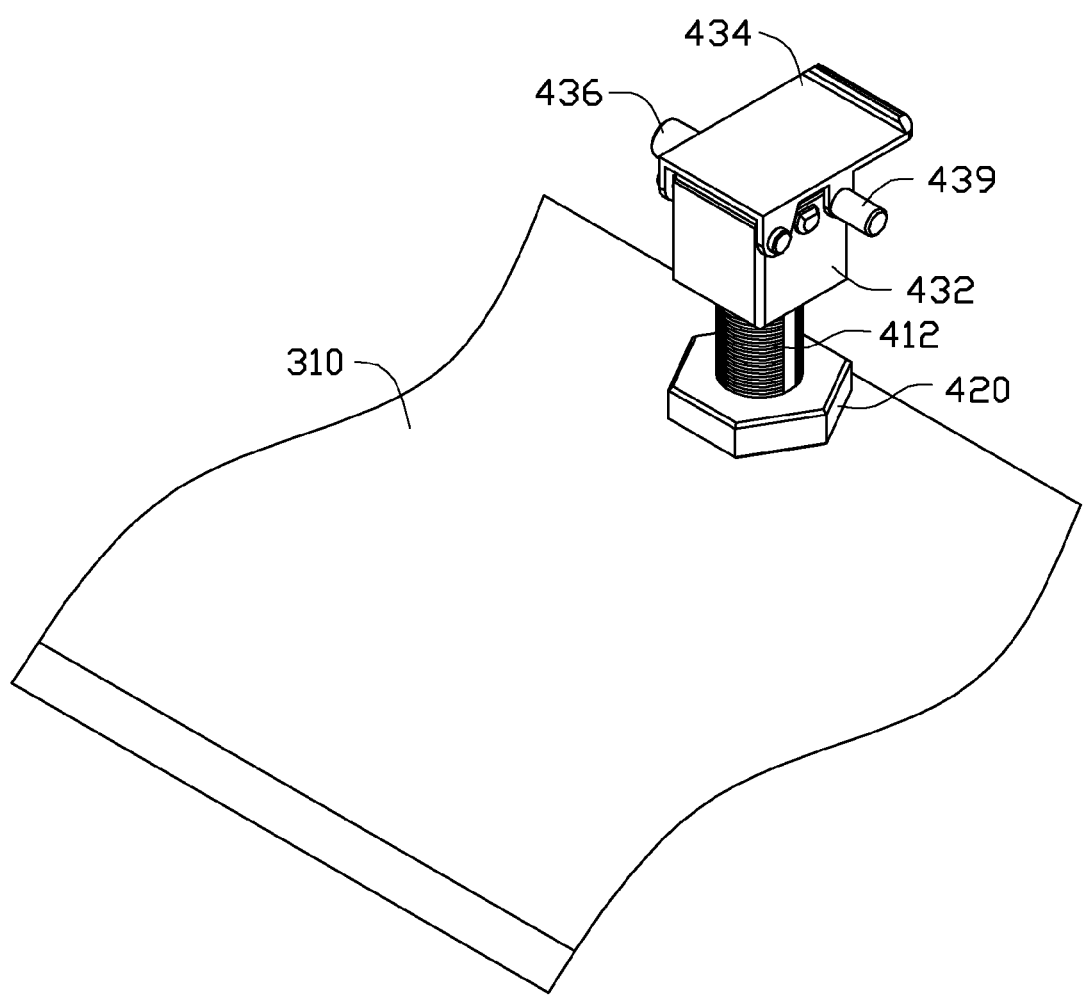
FIG. 4 is a partial assembly view of the measuring device of FIG. 2.

Referring to FIG. 4, in assembly, first, the bracket 30 is fixed to the base 10. Second, the electronic scale 20 is secured to the base 10 and beyond the supporting plate 310. Third, one of the nuts 420 engages with the screw 412, and then, the screw 412 extends through the through hole 312 with the protrusions 314 being received in the limiting slots 415, and further the other nut 420 engages with the screw 412. Finally, the clipping plate 450 is rotatably secured to the shafts 238, and the body 432 is further fixed to an end of the screw 412 away from the operating button 416.

Figure 5:
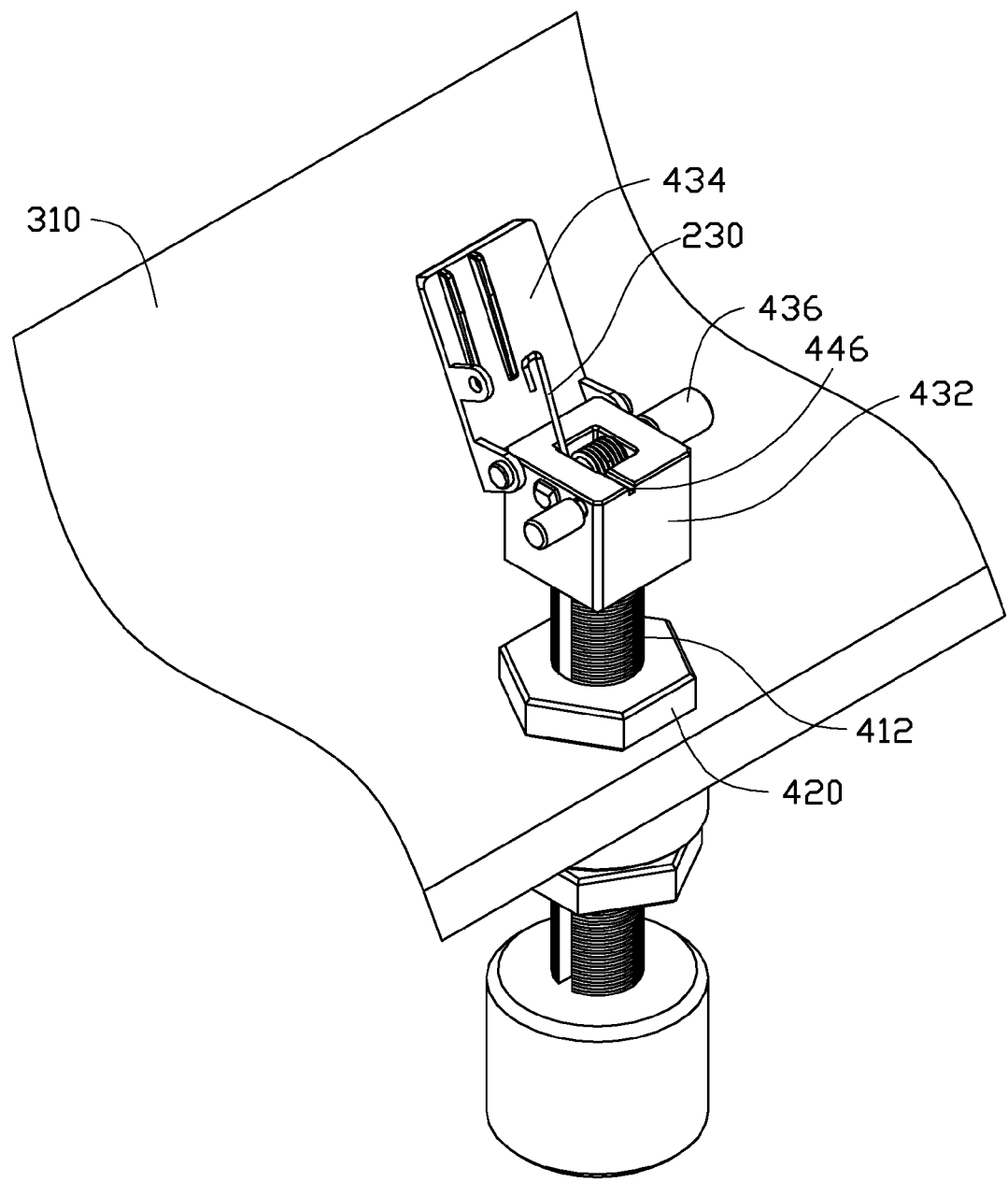
FIG. 5 is a partial perspective view showing the torsion spring is positioned to the measuring device of FIG. 4.

Referring to FIG. 5, to measure the torque of the torsion spring 200: first, the torsion spring 200 is received in the housing 432, with the positioning post 436 extending through the main body 210 and the first and second arms 220, 230 received in the receiving slot 446 and the limiting groove 454 respectively, and the torsion spring 200 is held to the holding mechanism 40. Second, by rotating the nuts 420, the holding mechanism 40 slides down driving the clipping plate 434 to depress the electronic scale 20, and the clipping plate 434 is resisted by the electronic scale 20 to rotate relative to the shaft 238 to deform the torsion spring 200. When the clipping plate 434 rotates parallel to the bottom case 444, the weight value W displayed on the scale 20 is obtained, and the torque of the torsion spring 200 is calculated by multiplying the obtained W by the acceleration due to gravity.

When the measuring device 100 is not used to measure the torque of the torsion spring 200, the position post 436 is detached from the housing 432, and the torsion spring 200 is removed. At this time, the clipping plate 434 is rotated parallel to the bottom case 444, and the limiting post 439 is inserted into the limiting hole 452 and the latching hole 435 to latch the clipping plate 434 to the housing 432, to prevent the clipping plate 434 from contacting with the electronic scale 20.

It is to be understood, even though information as to, and advantages of, the present embodiments have been set forth in the foregoing description, together with details of the structures and functions of the present embodiments, the disclosure is illustrative only; and that changes may be made in detail, especially in the matters of shape, size, and arrangement of parts within the principles of the present embodiments to the full extent indicated by the broad general meaning of the terms in which the appended claims are expressed.

What is claimed is:

1. A measuring device for measuring the torque of a torsion spring, comprising:
   a base;
   an electronic scale secured to the base;
   a supporting plate fixed to the base; and
   a holding mechanism slidably secured to the supporting plate, the holding mechanism comprising:
   a screw slidably secured to the supporting plate;
   two nuts engaging with the screw and arranged at opposite sides of the screw; and
   a holding portion for holding the torsion spring;
   wherein the nuts are operated to adjust the height of the screw relative to the supporting plate, to drive the torsion spring to depress the electronic scale, and the electronic scale displays a weight value for calculating the torque of the torsion spring.

2. The measuring device of claim 1, wherein the torsion spring comprises a hollow main body and two arms extending from opposite ends.

3. The measuring device of claim 2, wherein the holding mechanism comprising a housing and a clipping plate rotatably secured to the housing, the housing is fixed to an end of the screw and is for receiving the main body, an end of the housing away from the screw defines a limiting slot for receiving one of the arms, and the clipping plate defines a limiting groove for receiving the other one of the arms.

4. The measuring device of claim 3, wherein two shafts are secured to the housing, the clipping plate is rotatably coupled to the shafts.

5. The measuring device of claim 4, wherein two spaced flanges are secured to the clipping plate to define the limiting groove, the flanges extends in a direction perpendicular to the shafts.

6. The measuring device of claim 4, wherein the housing further defines an opening communicating with the limiting slot, the opening allows the main body to be received in the housing.

7. The measuring device of claim 4, wherein the holding portion further comprises a positioning post, the positioning post is parallel to the shafts and is detachably secured to the housing.

8. The measuring device of claim 7, wherein the positioning post is used for extending through the main body to hold the torsion spring to the holding portion.

9. The measuring device of claim 4, wherein the housing defines a latching hole, the clipping plate defines a limiting hole corresponding to the latching hole.

10. The measuring device of claim 9, wherein the holding mechanism further comprises a latching post, the latching post is capable of being inserted into the latching hole and the limiting hole to latch the clipping plate to the housing.

11. The measuring device of claim 1, wherein the supporting plate define a through hole for receiving the screw, at least one protrusion is secured to an inner side of the through hole.

12. The measuring device of claim 11, wherein the screw further defines at least one limiting slot extending in a lengthwise direction thereof, the at least one limiting slot engages with the at least one protrusion to prevent the screw from rotating when the screw slide relative to the supporting plate.

13. The measuring device of claim 1, wherein the torque of the torsion spring is obtained by multiplying the weight value displayed on the electronic scale by the acceleration due to gravity.

\* \* \* \* \*